United States Patent [19]

Cipris et al.

[11] Patent Number: 4,782,332
[45] Date of Patent: Nov. 1, 1988

[54] LUBRICANT OIL MONITORING SYSTEM, SENSOR FOR MONITORING LUBRICANT OIL QUALITY AND METHOD OF MANUFACTURING SENSOR FOR MONITORING LUBRICANT OIL QUALITY

[75] Inventors: Divna Cipris, Millburn; Arthur T. Walsh, Morris Plains, both of N.J.

[73] Assignee: Allied-Signal Inc., Morris Township, Morris County, N.J.

[21] Appl. No.: 67,982

[22] Filed: Jun. 29, 1987

[51] Int. Cl.⁴ ............................................. G08B 21/00
[52] U.S. Cl. ...................................... 340/603; 340/59
[58] Field of Search .......................... 340/603, 631, 59; 73/61.1 R, 53, 64

[56] References Cited

U.S. PATENT DOCUMENTS

4,464,070 2/1987 Yasuhara et al. ................. 340/59 X
4,628,252 12/1986 Terhune et al. ................. 340/603 X
4,675,662 6/1987 Kondo et al. ...................... 340/59 X Primary Examiner—Stewart J. Levy
Assistant Examiner—Joseph W. Roskos
Attorney, Agent, or Firm—Anibal Jose Cortina; Gerhard H. Fuchs

[57] ABSTRACT

The invention relates to an improved sensor for use in-situ in an electrical circuit which sensor corrodes as a result of deterioration of the oil and provides a changing electrical current due to increased resistance resulting from said corrosion. The sensor preferably is a ceramic tube havign a first layer of electrolessly deposited nickel thereon with a second layer of electrolitically plated lead. Leads are attached to the ends of the tube and the sensor can then be employed in-situ in oil to, as a result of its corroding and change in resistivity, measure deteriorating oil quality.

12 Claims, 6 Drawing Sheets

FIG. 7
WEIGHT LOSS CORROSION MEASUREMENTS OF LEAD
GTX 10-40W - 7500 MILES

FIG. 8

LUBRICANT OIL MONITORING SYSTEM, SENSOR FOR MONITORING LUBRICANT OIL QUALITY AND METHOD OF MANUFACTURING SENSOR FOR MONITORING LUBRICANT OIL QUALITY

CROSS-REFERENCE TO RELATED APPLICATIONS

This application is related to copending application Ser. No. 067,983 concurrently filed herewith, whose disclosure is specifically incorporated by reference herein.

BACKGROUND OF THE INVENTION

This invention relates to a sensor for use in a sensor system for in-situ monitoring of lubricant oil quality and to a method of manufacturing the sensor. In this regard, this sensor is particularly adapted for use in the system of copending application referred to above.

As discussed in said copending application, lubricant oil in use in automotive applications or other combustion engine applications is subjected to an aging process as a result of its use in the engine operation. The exposure of oil to high temperature zones in the presence of $NO_x$, moisture and air are main factors contributing to chemical changes which decrease the oils lubricating effectiveness.

As a result of the this decrease in its effectiveness, detrimental effects may result on the engine parts, for example, accelerated corrosion.

In addition to the break up of the lubricant, corrosivity also increases as the oil ages because degradation products of various type accumulate. Accumulation of other contaminants will also occur simultaneously, including mineral acids such as sulfur, nitrogen and hydrohalic based acids, soot and water. The final result is an oil whose acidity, corrosivity and viscosity has substantially increased as it reaches the end of its useful life, which as previously indicated, can result in disastrous consequences when continued in use in an internal combustion engine.

Up until the filing of the above-referenced copending application, there had been no system or method of measuring the deterioration of oil in-situ in an automotive environment. The current practices of determining oil condition require laboratory measurement such as titration of total base numbers, i.e. TBN, which is defined as the number of miligrams of KOH required to neutralize all acidic constituents present in one gram of the sample of oil.

In accordance with the invention, a sensor element is provided particularly adapted for use in a system for example, in accordance with that described in copending application Ser. No. 067,983, which takes advantage of the corrosive effects of spent oil as a means of providing an electrically functioning indicator sensor. Thus in accordance with the invention, the problem of having to conduct oil testing in a laboratory environment is avoided.

SUMMARY OF THE INVENTION

In one aspect, the invention relates to a sensor for use in a system for in-situ monitoring of lubricant oil quality wherein the sensor is to be placed in continuous contact with the lubricant oil. The sensor itself comprises a non-conductive support having a film of conductive metal electrochemically deposited thereon in a manner such that leads can be attached to the film to complete a circuit, and the film being corrodable and of a thickness such that upon continuous contact with deteriorating lubricant oil it will corrode away and will break open or change conductivity of the circuit after a predetermined amount of deterioration of the oil.

In another aspect, the invention relates to an improvement in a sensor system for in-situ monitoring of lubricant oil wherein the sensor is arranged in a circuit in contact with the lubricant oil for supplying an electrical signal indicative of the lubricant oil deteriorating condition when the signal exceeds predetermined values. the improvement resides in the above-discussed sensor.

In yet still another aspect, the invention relates to a method of manufacturing the sensor which comprises the steps of electrolessly depositing a metal which is noncorrodable in spent oil on the surfaces of a ceramic tube having two ends. Thereafter, a layer of a metal corrodable in spent oil is electrolitically deposited on the electrolessly deposited layer. With this arrangement, leads can then be attached to the two ends of the tube and the sensor can then be employed in a circuit.

BRIEF DESCRIPTION OF THE DRAWINGS

Having briefly described the invention, the same will become better understood from the following detailed description, taken in conjunction with the attached drawings wherein.

DETAILED DISCUSSION OF THE INVENTION

Figure 1:
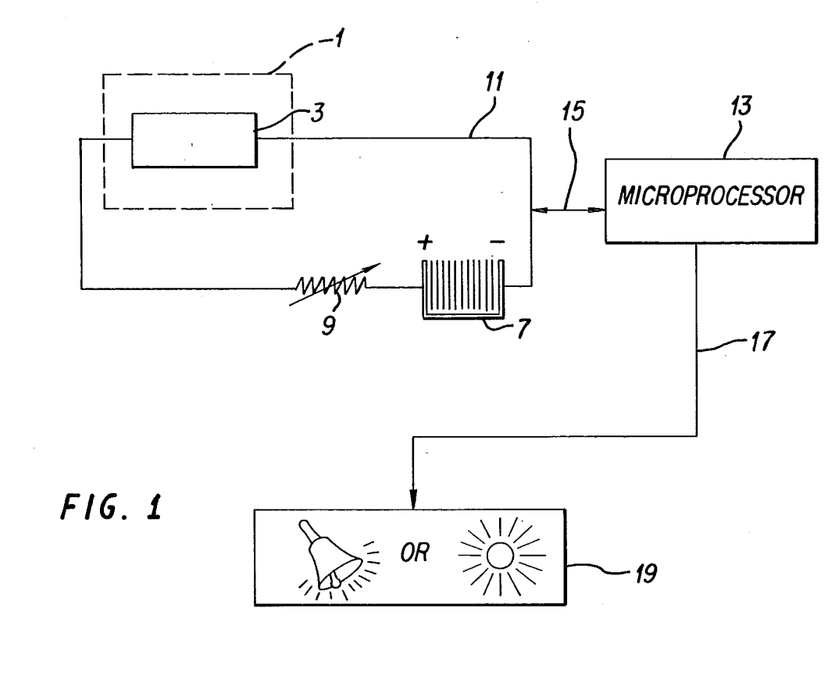
FIG. 1 is a general schematic diagram of the type of circuit in which the sensor in accordance with the invention would be employed in-situ.

In accordance with the invention, the sensor 1 is employed in circuit such as shown in FIG. 1. It is, as previously noted herein, and discussed in copending application Ser. No. 067,983, a sensor 1 which consists of a sensor element 3 employed in a circuit. The circuit is completed by electrical lines 11 which include therein a battery power supply 7 and a variable resistor 9 to adjust for specific oils in which the sensor is employed such that an appropriate signal can be obtained therefrom upon a change in resistance of the sensor due to corrosion caused by the oil with which it is in contact. The change in resistance or the electrical signal which flows through circuit 11 is passed by line 15 to a conventional microprocessor 13 of the type presently employed in automotive applications. Upon the signal through circuit 11 exceeding predetermined perimeters, the microprocessor 13 then activates a warning panel 19 through line 17. The warning panel can consist of an audio or a visual indication as shown in FIG. 1.

Figure 5:
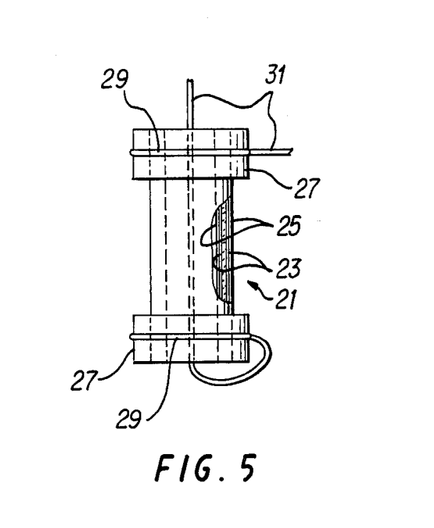

As to the sensor itself, it is generally shown in FIG. 5 with the steps of assembling a sensor shown in FIGS. 2-5. Preferably the sensor is a ceramic tube 21 having an outer surface and an inner surface shown in dashed lines as 21a. In the manufacture thereof, initially a thin layer 23 of a metal which is not corrodable in spent oil is electrolessly deposited in a conventional manner on the inner and outer surfaces of the ceramic tube. Although nickel is the preferred material due to cost and adherence to the ceramic tube, it is noted that various other materials such as copper, platinum, gold, silver or other metals which can be electrolessly deposited on the ceramic tube 21 can be substituted for nickel. Preferably the nickel is deposited in a thin layer of, for example, approximately 0.5 micron.

Thereafter, a layer 25 of a metal corrodable in spent oil is electrolitically deposited in a conventional manner on the nickel 23. In this regard, the layer is preferably lead or lead alloy but the lead or lead alloy can be replaced with such corrodable materials as zinc, tin or any other metal which is corrodable in spent oil. The electroplating process is conventional and well known to those of ordinary skill in the art. Further, the layer of lead is preferably about 5 micron, i.e. sufficient to provide enough lead to corrode over a sufficiently long period of time to allow proper measurement of the deteriorating quality of the oil.

At the ends of the tube 21, the lead or lead alloy is further deposited to a thickness as shown at 27 of preferably 50 micron to allow attachment of spring clip 29 at each end to which are attached leads 31, which are all made of nickel. Upon the spring clips 29 being attached to the lead, due to the soft nature of the lead, they preferably compress into the lead and are securely held on the sensor.

In the manufacture of the sensor, it is noted that in order to prepare conductive metal films on nonconductive surfaces, i.e., nickel and ceramic, the nonconductive surface has to be adequately pretreated. The pretreatment may consist of one or more steps and as noted above, the common way of metal deposition on nonconductive surfaces is done by electroless plating. Since not all metals can be electrolessly plated and some only with substantial difficulties, with lead falling in this category, the first layer is, as noted previously an electrolessly deposited nickel layer. Thereafter, since nickel is the added surface layer, the lead can then be commonly electrolitically deposited on the nickel.

Figure 2:
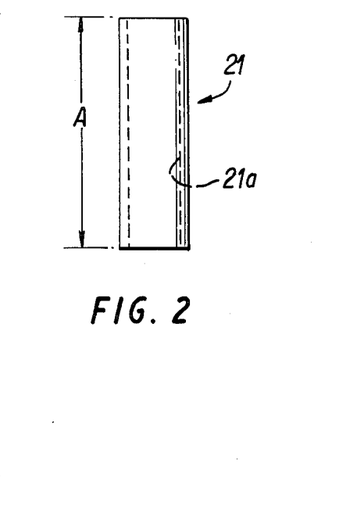
FIGS. 2-5 illustrate sequentially different steps in the manufacture of the sensor in accordance with the invention, with the sensor finally being illustrated in assembled form in FIG. 5.
Figure 3:
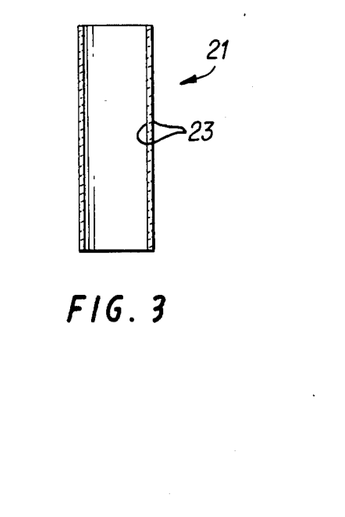
Figure 4:
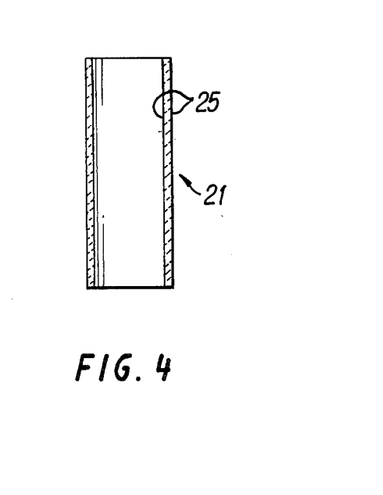

For the sensor to work as expected, which is as a fuse, which will "open" upon corrosion attack, or which will signal, by a change in resistivity, its change in condition, the resistance of the deposited lead layer has to be substantially lower than that of the underlying nickel. Since the conductivity of nickel is higher than that of lead and lead is used as a thin film which may be only as thin as 1-2 micron but preferably up to 5 micron, it is clear that the thickness of the underlying nickel has to be extremely small, which, as noted previously, is preferably less than 0.5 micron. Of course, in other specific applications, thicker films may be warranted. In accordance to the specific embodiments which as noted previously with respect to the preferred thicknesses of lead and nickel, the resistivity of the lead will be less than 1 ohms and the nickel film will have resistivity of 200-2,000 ohms. With respect to the size of the sensor itself, it is preferably as indicated at A in FIG. 2 is about 2 cm long with a diameter B of approximately 0.36 cm.

In accordance with the deteriorating properties of the lead layer, the microprocessor 13 can then be programmed within predetermined parameter such that when a certain amount of current flow is received from the sensor, it can trigger activation of the panel 19.

Although the sensor has been described as preferably a ceramic tube covered with thin high resistance layer of nickel overlayed with the low resistance layer of pure lead, other configurations can be employed and will be equivalent to the preferred embodiment of this invention. For instance, it will be readily apparent to one of ordinary skill in the art that a small ceramic plate can be used as the support of the sensing element instead of the tubular structure, with all the other construction elements remaining essentially the same.

Having generally described the invention, the same will become further better understood from the following illustrative detailed examples.

EXAMPLE 1

Ceramic tubes of dimension of 2 cm×0.36 cm in diameter were prepared for electrolytic lead deposition in two steps. Initially, an activation process was followed and thereafter, nickel was electrolessly deposited thereon. The activation process consisted of thorough cleaning in boiling concentrated potassium hydroxide for 1 hour and thereafter rinsing with distilled water and drying in a vacuum oven at 120° C. for 1 hour. After removal from the oven and cooling to room temperature, the tubes were placed in dilute, i.e. 1%, aqueous palladium chloride solution for 2-3 minutes and subsequently rinsed with distilled water. Palladium chloride was reduced with dilute, i.e. 1-2% aqueous, hydrazine solution having palladium nuclei deposited on the ceramic tube.

Palladium activated tubes were electrolessly nickel plated at 60° C. from the following aqueous solution:

30 g/liter nickel chloride
30 g/liter sodium citrate
10 g/liter sodium hypophosphate The tubes were continuously monitored for resistance until values measured across reached between 200-2000 ohms. A resistance of approximately 800 ohms corresponds to a nickel layer of about 0.5 micron thickness.

Thereafter, lead was electrolytically plated using a 50% aqueous lead tetrafluoroborate electrolyte at room temperature. The nickel plated tube was used as a cathode and a platinum screen as an anode. Current density was kept constant at 0.1 amp/cm$^2$ until desired thickness of the lead was obtained.

While the conditions cited in this Example have produced good quality films, variable conditions, based on the same principle, can also be utilized. This includes possible variations in plating solution concentration, temperature current density and time of deposition. Thus, both the film thickness and the film quality can be easily manipulated, by manipulating the deposition conditions.

The original deposit of lead on the tube had a very dull finish. Since lead is an extremely ductile metal, this dull finish was easily smoothed to a very bright finish by wetting a soft paper towel or cloth with acetone and rotating the tube inside of the towel while applying a slight even pressure on the tube.

Following the above general procedure, a number of ceramic tubes were covered with lead with a corresponding lead layer resistance in the range of approximately 0.05 to 0.10 ohm/cm. Resistance of the underlying nickel was typically 300 to 450 ohms.

EXAMPLE 2

Using the procedure described in Example 1 for lead deposition, lead deposited tubes were then clamped with nickel rings, to which nickel wires were attached. The assembled sensor then had a resistance which was somewhat increased because it included contacts and electrical lead resistances. The sensors were immersed in spent oil at elevated temperature, connected to a power source and a monitoring device, and corrosion of lead was followed in different cases by a either an increase in the sensor resistivity, or "turning off" of a small electrical bulb connected in the series. Testing temperature of the oil was typically 130° C. In a typical example, the sensor resistance was 0.80 ohms, with an underlying nickel layer resistance of 450 ohms. After corroding in CAM II 20-50 W lubricant oil which had been used for 277 hours previously in a laboratory engine test, for 72 hours in the spent oil at 130° C., the sensor resistance increased to 100 ohms, at which point the test was discontinued.

EXAMPLE 3

The same as Example 2 was conducted, only the initial sensor's resistance was 1 ohm and the resistance of the underlying nickel was 380 ohms. After corroding in CAM II 20-60 W oil which had been placed in spent condition after 277 hours in laboratory engine tests, at 130° C. for 38 hours, the final sensor resistance was 50 ohms.

EXAMPLE 4

The same as Example 3 was conducted but the oil, CAM II 20-50 W, was used for 150 hours in laboratory engine tests prior to testing. The test was performed at 130° C. The sensor's resistance went from less than 1 ohm to 50 ohms in 150 hours.

EXAMPLE 5

The same as Example 4, but the oil used for testing was GTX 10-40 W, used in a passenger car, which was driven for 7500 miles on the road under normal operating conditions. The sensor's resistance changed from an initial value of less than 1 ohm to 50 ohms in 72 hours.

EXAMPLE 6

The same as Examples 1-6 but the oil, CAM II 20-50 W was "as sold", i.e., fresh. The sensor was immersed in fresh oil at 130° C. for over two weeks. The sensor's resistance remained virtually unchanged from its original value of approximately 1 ohm. This test was repeated a number of times with the same results.

EXAMPLE 7

The same as Example 6, but the oil tested was GTX 10-40 W. The temperature was 130° C. The resistance of assembled lead sensor remained unchanged for over two weeks upon immersion in this oil. The test was repeated several times with the same results.

EXAMPLE 8

Figure 6:
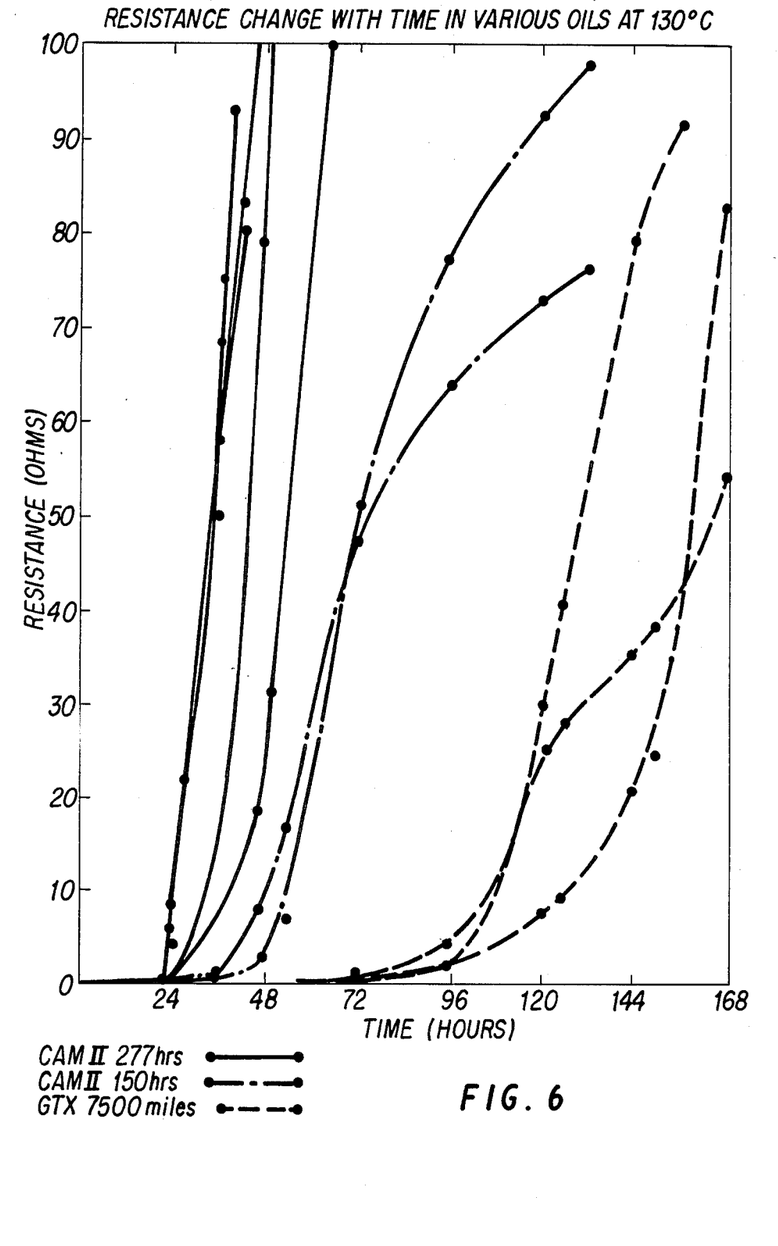
FIG. 6 is a graph illustrating the change in resistance of various sensors having current applied therethrough after immersion in spent oils for predetermined periods of time.

Examples 1-7 were repeated a number of times. The starting lead film resistance was approximately 0.1 ohms in all cases and the resistance of the assembled sensors was less than 1 ohm. The test results are shown in attached FIG. 6.

EXAMPLE 9

Figure 7:
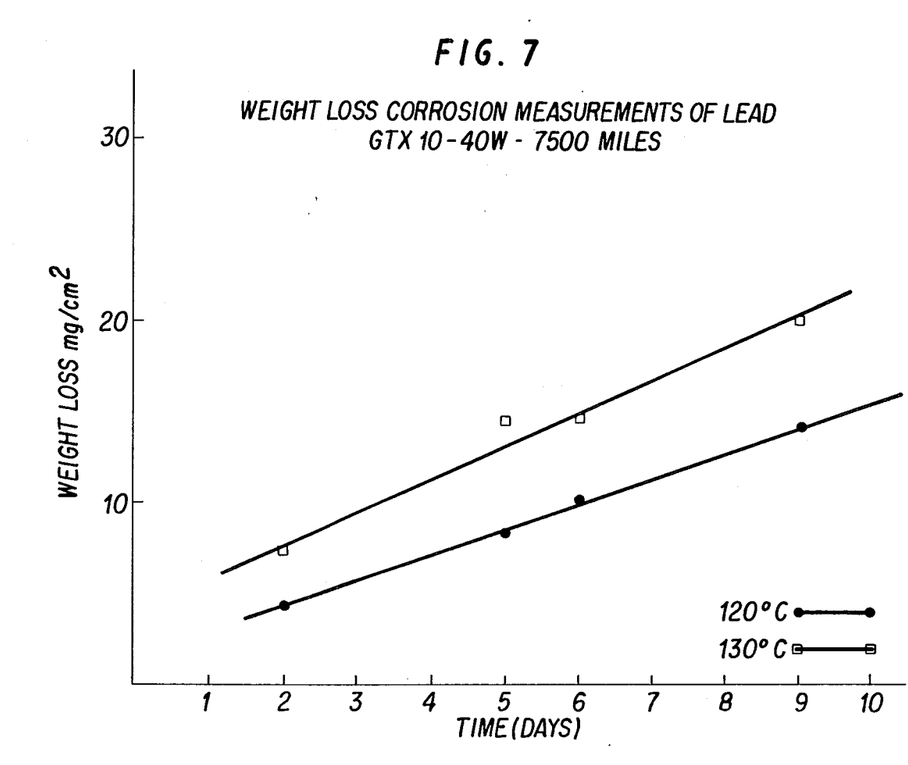
FIGS. 7-9 are graphs, respectively, showing testing results of weight loss corrosion measurements of lead strips, functionally representative of the sensor of the invention, after immersion in different spent oils for differing amounts of time.

In this example, commercial lead foil strips having dimensions of $0.1 \times 10 \times 50$ cm, to functionally stimulate the sensor of the invention, were corroded in fresh and spent oil used for 7500 miles on the road, (GTX 10-40 W). The rate of corrosion was followed by weight loss of the lead foil strips. The oil temperature used in these tests was 120° C. and 130° C. respectively. The results are plotted as weight loss of lead in mg per $cm^2$ vs. time in days in FIG. 7. Weight of lead in fresh oil remained virtually unchanged over 3 weeks.

EXAMPLE 10

Figure 8:
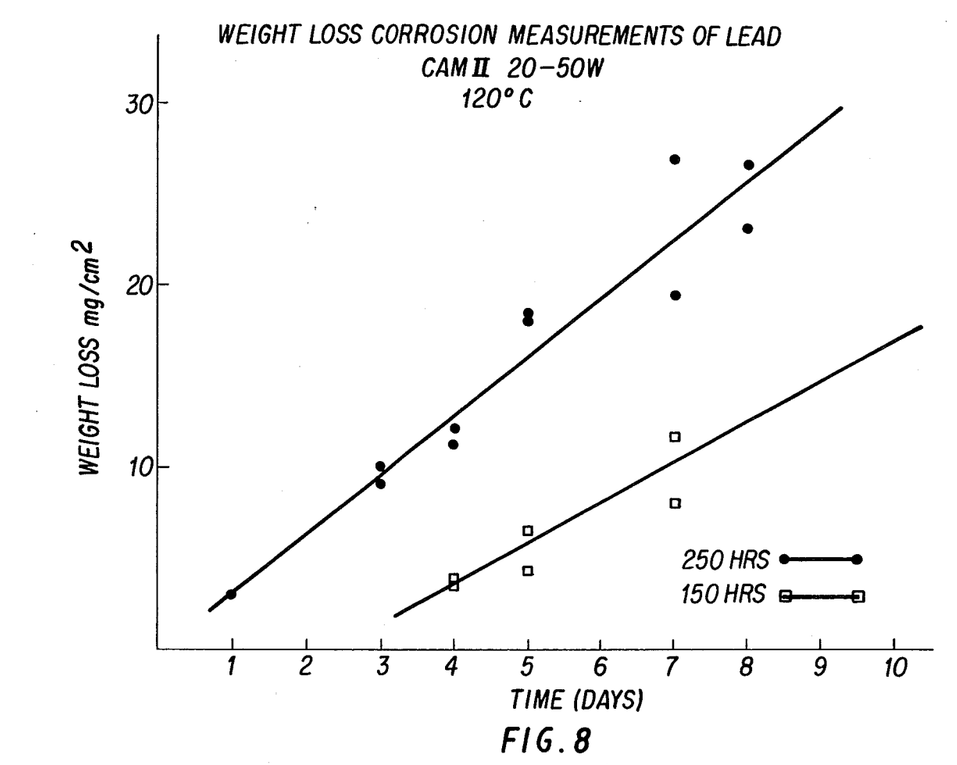
Figure 9:
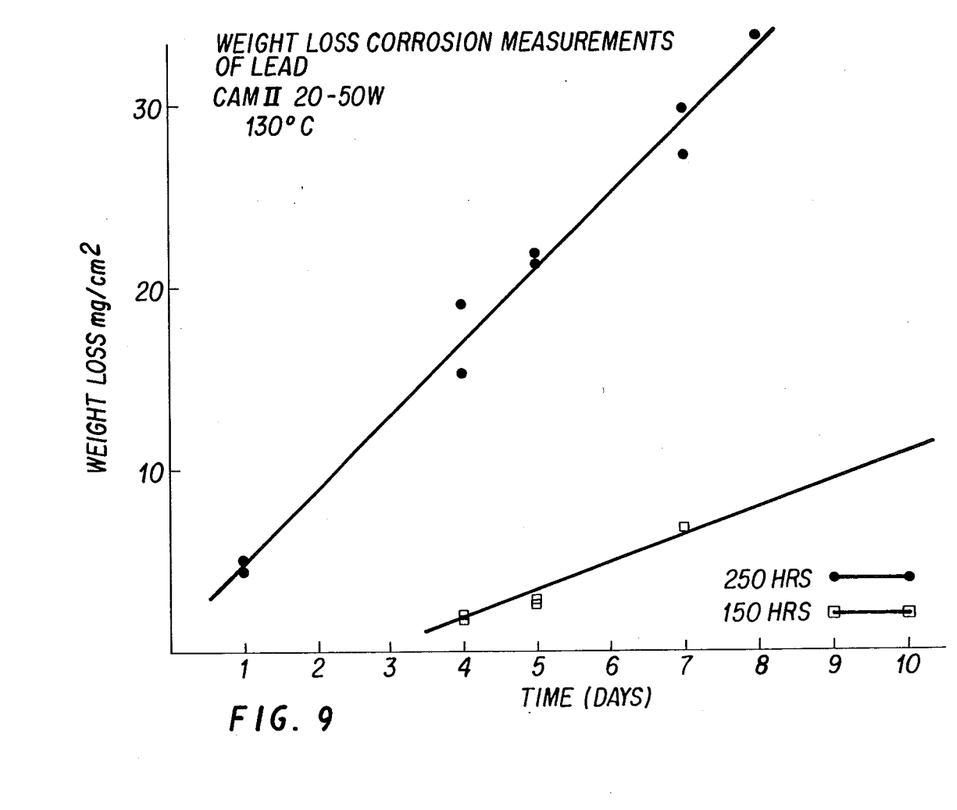

The same as Example 9, but the oil used in the tests was CAM II 20-50 W "spent" oil used for 150 hours and 250 hours in laboratory engine tests, respectively. The results are plotted in FIG. 8 and FIG. 9. The weight of lead in the fresh oil remained the same for the duration of the experiment, i.e., over 3 weeks.

What is claimed is:

1. In a sensor system for in-situ monitoring of lubricant oil quality wherein sensor means is arranged in a circuit in contact with said lubricant oil for supplying an electrical signal indicative of the lubricant oil deteriorating condition when said signal exceeds predetermined values, the improvement wherein said sensor comprises: a non-conductive support having a film of conductive metal electrochemically deposited thereon in a manner such that leads can be attached to said film to complete said circuit, said film comprising a first layer of a metal which is non-corrosible in spent oil which has been electrolessly deposited on the surfaces of said support and a second layer of metal corrosible in spent oil which has been electrolitically deposited on said electrolessly deposited layer and said second layer being of a thickness such that upon continuous contact with deteriorating lubricant oil it will corrode away and will break open or change conductivity of said circuit after a predetermined amount of deterioration of said oil.

2. A sensor system as in claim 1 wherein said non-conductive support is a ceramic tube having two ends.

3. A sensor system as in claim 2 wherein said first layer is at least one of copper, platinum, gold, silver and nickel, and said second layer is at least one of tin, zinc, lead and lead alloy.

4. In a sensor system for in-situ monitoring of lubricant oil quality wherein sensor means is arranged in a circuit in contact with said lubricant oil for supplying an electrical signal indicative of the lubricant oil deteriorating condition when said signal exceeds predetermined values, the improvement wherein said sensor comprises: a non-conductive support comprised of a ceramic tube having two ends, with a film of conductive metal electrochemically deposited thereon in a manner such that leads can be attached to said film to complete said circuit, said film comprising a first layer of Ni which has been electrolessly deposited on the exterior surfaces of said ceramic tube and a second layer of lead or lead alloy which has been electrolitically deposited on said layer of Ni, and said second layer being of thickness such that upon continuous contact with deteriorating lubricant oil it will corrode away and will break open or change conductivity of said circuit after a predetermined amount of deterioration of said oil.

5. A sensor system as in claim 4 wherein said sensor is about 2 cm in length and about 0.36 cm in diameter, with Ni layer deposited at a thickness of about 0.5 micron and the lead or lead alloy layer deposited at a thickness of about 5 micron.

6. A sensor system as in claim 5 further comprising leads attached to respective ends of the tube.

7. A sensor for use in a system for in-situ monitoring of lubricant oil quality wherein said sensor is to be placed in continuous contact with said lubricant oil, the sensor comprising: a non-conductive support having a film of conductive metal electrochemically deposited thereon in a manner such that leads can be attached to said film to complete a circuit, said film comprising a first layer of a metal which is non-corrosible in spend oil which has been electrolessly deposited on the surfaces of said support and a second layer of metal corrosible in spent oil which has been electrolitically deposited on said electrolessly deposited layer, and said second layer being of a thickness such that upon continuous contact with deteriorating lubricant oil it will corrode away and will break open or change conductivity in a circuit in which it is used after a predetermined amount of deterioration of said oil.

8. A sensor as in claim 7 wherein said non-conductive support is a ceramic tube having two ends.

9. A sensor as in claim 8 wherein said first layer is at least one of copper, platinum, gold, silver and nickel, and said second layer is at least one of tin, zinc, lead and lead alloy.

10. A sensor for use in a system for in-situ monitoring of lubricant oil quality wherein said sensor is to be placed in continuous contact with said lubricant oil, the sensor comprising: a non-conductive support comprised of a ceramic tube having two ends, and having a film of conductive metal electrochemically deposited thereon in a manner such that leads can be attached to said film to complete said circuit, said film comprising a first layer of Ni which has been electrolessly deposited on the exterior surfaces of said ceramic tube and a second layer of lead or lead alloy which has been electrolitically deposited on said layer of Ni, and said second layer being of a thickness such that upon continuous contact with deteriorating lubricant oil it will corrode away and will break open or change conductivity of said circuit after a predetermined amount of deterioration of said oil.

11. A sensor as in claim 10 wherein said sensor is about 2 cm in length and about 0.36 cm in diameter, with Ni layer deposited at a thickness of about 0.5 micron and the Pb layer deposited at a thickness of about 5 micron.

12. A sensor as in claim 11 further comprising leads attached to respective ends of the tube.

* * * * *